United States Patent
Pridgen

(10) Patent No.: US 7,147,875 B2
(45) Date of Patent: Dec. 12, 2006

(54) METHOD AND COMPOSITION FOR RELIEVING SYMPTOMS OF ARTHRITIS AND GOUT USING FRUIT OF MIRACLES

(76) Inventor: John H. Pridgen, 1647 Union St., Apt. 4F, Brooklyn, NY (US) 11213

( * ) Notice: Subject to any disclaimer, the term of this patent is extended or adjusted under 35 U.S.C. 154(b) by 44 days.

(21) Appl. No.: 11/034,368

(22) Filed: Jan. 11, 2005

(65) Prior Publication Data

US 2005/0158410 A1    Jul. 21, 2005

Related U.S. Application Data

(60) Provisional application No. 60/537,335, filed on Jan. 20, 2004.

(51) Int. Cl.
*A61K 36/752* (2006.01)

(52) U.S. Cl. .................. 424/736; 424/765; 424/777
(58) Field of Classification Search .................... None See application file for complete search history.

(56) References Cited

OTHER PUBLICATIONS

US Dept. of Agriculture, USDA Database for the Flavonoid Co, Mar. 2003.
Warner, Arthritis Advances:Top 10 of 2004, www.foxnews.com/story/0,2933,140796,00.htm, Dec. 8, 2004.
wholehealthmd.com, Supplements, Cherry Fruit Extract, www.wholehealthmd.com/refself/substances_view/1,1525,10015,00.html; Dec. 6, 2004.
Medical Encyclopedia, Chronic Gouty Arthritis, www.NLM.Nlh.gov/medlineplus/ency/article/000424.htm, Dec. 2, 2004.

*Primary Examiner*—Susan Coe Hoffman

(57) ABSTRACT

A method and composition for treating gout and arthritis, particularly gouty arthritis and rheumatoid arthritis. The composition is a liquid mixture of the liquid portion of three different suspensions. Each suspension is a mixture of alcohol solvent and either apple peels, banana peels, or orange peels. The composition is prepared by allowing each of the fruit peels and the alcohol solvent to sit enclosed in a container for approximately six months and then mixing the three containers to obtain the ointment and then topically applied the ointment to the affected area of the skin. Swelling and pain are reliably eliminated for many months. In a preferred embodiment, the alcohol content of the containers are monitored and replenished if they decline.

14 Claims, No Drawings

METHOD AND COMPOSITION FOR RELIEVING SYMPTOMS OF ARTHRITIS AND GOUT USING FRUIT OF MIRACLES

PRIORITY INFORMATION

This nonprovisional patent application is a continuation of pending U.S. provisional patent application No. 60/537,335 entitled Fruit of Miracles filed Jan. 20, 2004 by Applicant John H. Pridgen.

FIELD OF THE INVENTION

The field of this invention is treatments for arthritis and gout, and more particularly, treatments that relieve the symptoms of these diseases using natural ingredients.

BACKGROUND OF THE INVENTION AND DISCUSSION OF THE PRIOR ART

According to a December 2004 press release from the Arthritis Foundation, arthritis is the nations's number one cause of disability. Among the types of arthritis that affect large numbers of Americans are rheumatoid arthritis and gouty arthritis.

Acute gouty arthritis is an attack of a metabolic disease marked by uric acid deposits in the joints. The disorder is painful, especially in the joints of the feet and legs.

Gout is caused by a defect in metabolism that results in an overproduction of uric acid or a reduced ability of the kidney to eliminate uric acid. The exact cause of the metabolic defect is unknown. In acute gouty arthritis, symptoms develop suddenly and usually involve only one or a few joints. The pain frequently starts during the night and is often described as throbbing, crushing, or excruciating. The joint appears infected with signs of warmth, redness, and tenderness. The attacks of painful joints may subside in several days, but may recur at irregular intervals. Subsequent attacks usually have a longer duration. Some people may progress to chronic gouty arthritis, while others may have no further attacks.

The symptoms of gout include joint pain that affects one or more joints (e.g. hip pain, knee pain, ankle pain, foot pain, shoulder pain, elbow pain, wrist pain, hand pain, or pain in other joints). The great toe, knee, or ankle joints are most often affected. Other symptoms include joint swelling of the affected joints, stiffness of the joint, warm and red joints, fever, skin lumps.

Generally, adequate treatment of acute gout attacks allows people to live a normal life. However, the acute form of the disease may progress to chronic disease. Since uric acid is normally eliminated by the kidneys, chronic gout may lead to the formation of uric acid kidney stones. An attack of chronic gout is similar to an attack of acute gouty arthritis. Symptoms come on suddenly, usually involving only one or a few joints. The pain frequently starts during the night and is often described as throbbing, crushing, or excruciating. The affected joints show signs of warmth, redness, and tenderness. The pain tends to subside within several days. Chronic gout attacks, however, occur more often.

There is no known cure for gout or arthritis. The goals of treatment are mainly to stop the pain and inflammation associated with the initial attack, and to prevent future attacks.

Known drugs include colchicine, which is effective in reducing the pain, swelling, and inflammation associated with acute gout attacks. The pain often subsides within 12 hours of starting treatment, and is completely relieved in 48 hours. The medication works by decreasing the inflammation caused by uric acid crystals within the joint. However, it does not decrease the uric acid levels in the bloodstream. Daily use of colchicine or allopurinol helps prevent future attacks. Non-steroidal anti-inflammatory drugs (NSAIDs) can be very effective in treating the pain and inflammation of an acute gout attack if taken soon after symptoms start. Corticosteroids can also be very effective, although it requires that a doctor inject the inflamed joint with steroids to relieve the pain. Long term use of corticosteroids can cause damage to bones and have many other side effects.

Although biologic drugs like Rituxan, Abatacept, and methotrexate have shown some promise in treating rheumatoid arthritis these drugs do not provide complete relief or fully stop the progression of the disease. More importantly, they have side effects, as all drugs do.

There are dietary changes that may be prescribed for gout and/or arthritis either by doctors or by alternative medicine promoters. For example, a diet low in purines may be prescribed by doctors also in fighting arthritis. Organ meats, beer, wine, and certain types of fish contain high levels of purines. Increased fluid intake prevents the formation of kidney stones. Alternative medicine sources also recommend drinking cherry extract concentrate because it "may" prevent gout and lessen arthritis-related pain and inflammation. As with all dietary programs, it is hard to get a person to stick to them, particularly when there are no quantitative recommendations. Furthermore, the dietary changes may depend upon each person's eating habits and taste. Moreover, the dietary changes also have to fit with other special diets that a patient may have committed to. In general, proposed dietary changes are not looked to for curing arthritis or gout.

There has been no known reliable way of obtaining virtually complete relief from the symptoms of arthritis and gout over a long period of time, i.e. years, and particularly with no side effects. There is a compelling need for a natural remedy that reliably and fully relieves the symptoms of gout and arthritis without side effects over an extended period of time.

SUMMARY OF THE PRESENT INVENTION

A method and composition for treating gout and arthritis, particularly gouty arthritis and rheumatoid arthritis. The composition is a liquid mixture of the liquid portion of three different suspensions. Each suspension is a mixture of alcohol solvent and either apple peels, banana peels, or orange peels. The composition is prepared by allowing each of the fruit peels and the alcohol solvent to sit enclosed in a container for approximately six months and then mixing the three containers to obtain the ointment and then topically applied the ointment to the affected area of the skin. Swelling and pain are reliably eliminated for many months. In a preferred embodiment, the alcohol content of the containers are monitored and replenished if they decline.

IMPORTANT OBJECTS AND ADVANTAGES

The following important objects and advantages of the present invention are:
(1) to provide a method of treating rheumatoid arthritis;
(2) to provide a method of treating gouty arthritis;
(3) to provide a method of treating gout;
(4) to provide a composition of matter, particularly in the form of an ointment, useful in the treatment of the symptoms of gout (5) to provide a composition of matter, particularly in the form of an ointment, for treating the symptoms of arthritis, particularly gouty arthritis and rheumatoid arthritis;

(6) to provide such a method and ointment that does not have significant side effects;

(7) to provide such a method and ointment that can be prepared easily by laypersons even at home;

(8) to provide such a method and ointment that stops the progression of gout and arthritis;

(9) to provide a precise method of creating an ointment that can relieve the symptoms of gout;

(10) to provide a precise method of creating an ointment that relieve the symptoms of gouty arthritis;

(11) to provide a precise method of creating an ointment that can relieve the symptoms of rheumatoid arthritis;

(12) to provide such a method that provides relief from the symptoms of arthritis and gout for approximately half a year at a time;

(13) to provide such a method that when re-applied whenever symptoms appear can effectively relieve the symptoms over many years;

(14) to provide a method and composition for the treatment of gout and arthritis that is applied topically to the skin of a patient; and

(15) to provide a method and composition fir the relief of the symptoms of gout and arthritis that is easy to apply.

DETAILED DESCRIPTION OF THE PREFERRED EMBODIMENT

The method of the present invention will now be described in detail, including the preferred embodiment.

Either by hand or in the case of an apple, using an instrument such as a peeler or a knife, peel a quantity of apples, bananas and oranges. Place the peels of approximately six medium sized apples into a container, preferably a container that holds a measure equal to one quart. In a preferred embodiment, the stem of the apples was discarded and not used. Also, place the peels of approximately six medium sized ripe bananas into a similar container. Finally, place the peels of approximately six medium sized oranges in a similar container. Containers that are either smaller or larger than quart size may be also used, and other quantities of the peels of the apples, oranges and bananas can also be used, provided the above proportion is maintained between the quantity of peels and the size of the container, i.e. approximately six peels of a particular one of the above fruit for every quart of capacity of the container.

The next step in the method, which is typically although not necessarily done after placement of the peels into the container, involves adding an alcohol solvent to each of the containers until they are full. The preferred alcohol solvent is rubbing alcohol. Rubbing alcohol is defined as either 70 percent by weight isopropyl alcohol plus 30 percent water or else 70 percent by weight denatured ethyl alcohol. These two varieties of rubbing alcohol is widely available in any drug store.

In an alternative embodiment, instead of adding rubbing alcohol, add a different alcohol solvent, such as ethyl alcohol or isopropyl alcohol. It may be that other alcohol solvents may also work, but the resulting ointment may be safer with the rubbing alcohol, ethyl alcohol and isopropyl alcohol. In addition, these alcohol solvents, particularly rubbing alcohol, are readily available.

In the next step, allow the three containers to stand for at least approximately six months. Preferably, allow the three containers to stand for approximately six months. In a preferred embodiment, while the three containers are standing, monitor them and replenish the level of alcohol solvent when and if said level declines by an amount that is noticeable, for example through evaporation. "Approximately six months" as used herein shall mean between approximately 5 and a half months and approximately 6 and a half months. "Approximately five months" as used herein shall mean between approximately 4 and a half months and approximately five and a half months. The approximate six months period is not exact but applicant's experiments indicate that if the mixture is allowed to stand for approximately 4 to 5 months, the efficacy of the resulting ointment will be somewhat effective but will not be as potent. Furthermore, based on the experiments, if the mixture is left to stand for a period even shorter than approximately four months, the resulting ointment may not be particularly effective at all. It is believed that allowing the containers to sit for more than approximately six months will also result in an effective ointment.

The storage should occur under normal conditions of room temperature and humidity. However, it is believed based on experience of the applicant's experiments that the method of the present invention will work even if the storage occurs in a very dry or very humid room environment or even in temperatures that are significantly hotter or colder than room temperature.

For the next step of the method, after the approximately six months time period, filter out the liquid from each of the containers by separating the solid particles using any suitable technique such as pouring the contents of the container into an ordinary bowl-shaped kitchen instrument, such as a colander, that contains holes and collecting the clear liquid that falls through the holes. Then mix together the liquid obtained from each of the three containers and thoroughly stir the final mixture.

The resulting stirred final mixture is a liquid ointment that is very watery and does not smell from alcohol. Apply the liquid ointment generously to the affected areas of the skin topically using well known and simple methods. For example, dip a cloth in the ointment and soak it with the ointment and then apply the cloth directly on the affected area of the skin repeatedly and generously so that a generous amount of liquid is in contact with and is absorbed into the skin. In a preferred embodiment, this treatment is performed approximately twice a day. However, the present invention encompasses any method in which the treatment is performed between one and as many times a day as is necessary to cause significant amounts of the liquid composition to be absorbed by the body in the affected areas. Perform this treatment for as many days the symptoms remain. Symptoms of arthritis and gout should begin to be eliminated immediately and the relief should last for numerous months.

The exact mechanism for the relief that is obtained using the method and composition of the present invention is not known for certain. However, it has been posited as a possibility that the active ingredient in the ointment of the present invention is one or more flavonoids and possibly other organic molecules contained within the peels and attached fruit of the oranges, bananas and apples. These molecules are gradually extracted from the peels of the apples, bananas and oranges and dissolve in the rubbing alcohol. Oranges, apples and bananas are rich in certain flavonoids useful in rectifying the uric acid and/or other metabolic irregularities associated with gout and arthritis. Although flavonoids come in 4000 different varieties, the particular flavonoids found in apples, oranges and banana peels are believed, based on experience with the method and composition of the present invention, to be particularly useful in the treatment of gout and arthritis.

Applicant's experiments suggested that using the method and/or composition of the present invention with only apples, only bananas, only oranges or a combination of two of these fruit would not be effective and that all three were needed.

It is noted that the phrase "area of skin affected by arthritis" means an area of skin in which or under which symptoms of arthritis, such as pain, swelling, etc., are occurring. Similarly, the phrase "area of the skin affected by gout" means an area of the skin in which symptoms of gout, such as swelling, are occurring.

The Composition

The composition of the present invention is described as a mixture of three suspensions. In this description the term "suspension" is understood to mean a broad definition of a mixture having both solid and liquid components where the solid components are not all dissolved in the liquid components. The term "suspension" is thus not necessarily exactly equivalent to the typical English language definition of said term.

The composition of the present invention can be described as a liquid mixture, the mixture comprising:

approximately one third by volume liquid residue from a first suspension of orange peels in a first container filled with an alcohol solvent, the suspension having stood for at least approximately five (and in a preferred embodiment at least approximately six) months, and the first suspension having a proportion of peels of at least approximately six medium sized oranges per one quart of capacity of the first container, approximately one third by volume liquid residue from a second suspension of banana peels in a second container filled with an alcohol solvent, the second suspension having stood for at least approximately five (and in a preferred embodiment at least approximately six) months and the second suspension having a proportion of peels of at least approximately six medium sized banana per one quart of capacity of the second container, and approximately one third by volume liquid residue obtained from a third suspension of apple peels in a third container filled with an alcohol solvent, the third suspension having stood for at least approximately five (and in a preferred embodiment at least approximately six) months and the third suspension having a proportion of peels of at least approximately six medium sized apples per one quart of capacity of the third container.

In a preferred embodiment of the above composition, the first suspension is in a proportion of peels of approximately six medium sized oranges per one quart of capacity of the first container, the second suspension is in a proportion of peels of approximately six medium sized banana per one quart of capacity of the second container, and the third suspension is in a proportion of peels of approximately six medium sized apples per one quart of capacity of the third container.

In a preferred embodiment, the alcohol solvent in one or more of the three suspensions is rubbing alcohol. In a further preferred embodiment, the alcohol solvent in all three suspensions is rubbing alcohol. In an alternative embodiment, the alcohol solvent in all three suspensions is ethyl alcohol. In a further alternative embodiment, the alcohol solvent in one or more of the three suspensions is ethyl alcohol. In a further embodiment, the alcohol solvent in all three suspensions is isopropyl alcohol. In a further alternative embodiment, the alcohol solvent in one or more of the three suspensions is isopropyl alcohol.

In this patent application, the term "alcohol solvent" is used to denote the fact that the alcohol in the mixture or suspension presumably allows molecules that emanate from the sold peels to dissolve therein.

EXAMPLES

In each of the examples given below, the patient achieved the results described without the intervention of a physician. Furthermore in each of the examples below the composition utilized rubbing alcohol as the alcohol solvent. In addition, with respect to each of the examples below, in the preparation of the composition used therein each of the three containers stood for approximately six months. Furthermore, in each example the composition was applied in accordance with the method of the present invention. That is, the liquid ointment was placed in a cloth or absorbent material and after the cloth was soaked with the liquid ointment the cloth was applied to the skin so that a generous amount of liquid was in contact with the skin and was then absorbed into the skin. That treatment was repeated at least once a day until the symptoms disappeared.

Example I

A patient who was diagnosed by a physician as having gout and gouty arthritis for many years was treated using the method and composition of the present invention. The ointment of the present invention was applied to the patient on the areas of the skin where the patient felt pain, or had swelling. As a result of the treatment, swelling from gout went away. Joint pain was relieved. The first treatment caused such relief to last for approximately four to six months until symptoms reappeared. When joint pain and swelling resumed, the method and composition of the present invention were applied again and the symptoms were virtually eliminated again for a similar period of time. The appearance of symptoms followed by the immediate relief from the symptoms caused by the treatment of the present invention occurred continuously for well over ten years. No side effects were reported by the patient from the treatment.

Example II

A patient who was diagnosed by a physician as having gout and gouty arthritis for many years applied the ointment of the present invention on the affected areas of the skin that had swelling and pain. Swelling from gout was eliminated. Pain, particularly, pain in the joints of the patient were relieved. A large swelling on the big toe was relieved. The relief lasted at least approximately several months. When joint pain and swelling resumed, the method and composition of the present invention were applied again and the symptoms were virtually eliminated again for a similar period of time. This went on continuously for several years with no known side effects.

Example III

A patient who had joint pains in the ankle and was understood to be suffering from arthritis applied the ointment of the present invention on the affected areas of the skin. The joint pain went away for several months. When joint pain and swelling resumed, the method and composition of the present invention were applied again and the symptoms were virtually eliminated again for a similar period of time. This went on continuously for several years with no known side effects.

Other individuals achieved similar results from treatment using the method and composition of the present invention.

In this patent application, the term "six medium apple peels" means the peels from six medium sized apples. It can also include the quantity of apple peels roughly equal in weight or volume to the peels of six medium sized apples even if derived from, say, 8 smaller apples or 4 larger apples. Similarly, the phrase "six medium sized orange peels" means the peels from six medium sized oranges but it can also include the quantity of orange peels roughly equal in weight or volume to the peels of six medium sized oranges even if derived from, say, 8 smaller oranges or 4 larger oranges. Likewise, the term "six medium banana peels" means the peels from six medium sized bananas but it can also include the quantity of banana peels roughly equal in weight or volume to the peels of six medium sized banana even if derived from, say, 8 smaller bananas or 4 larger bananas.

It is to be understood that while the method and composition of this invention have been described and illustrated in detail, the above-described embodiments are simply illustrative of the principles of the invention. It is to be understood also that various other modifications and changes may be devised by those skilled in the art which will embody the principles of the invention and fall within the spirit and scope thereof. It is not desired to limit the invention to the exact construction and operation shown and described. The spirit and scope of this invention are limited only by the spirit and scope of the following claims.

What is claimed is:

1. An ointment used in the treatment of arthritis and/or gout, comprising,
    a liquid mixture, the mixture comprising
    approximately one third by volume of a liquid residue obtained by removing solid particles from a first suspension of orange peels in an alcohol solvent, the suspension having stood for at least approximately five months, and being in a proportion of peels of at least approximately six oranges per one quart of container containing the orange peels and alcohol solvent,
    approximately one third by volume liquid residue obtained by removing solid particles from a second suspension of quantity of banana peels in an alcohol solvent, the suspension having stood for at least approximately five months and being in a proportion of peels of at least approximately six banana per one quart of container containing the banana peels and alcohol solvent, and
    approximately one third by volume liquid residue obtained by removing solid particles from a third suspension of apple peels in an alcohol solvent, the suspension having stood for at least approximately five months and being in a proportion of peels of at least approximately six apples per one quart of container containing the apple peels and alcohol solvent.

2. The ointment of claim 1, wherein the first suspension has stood for at least approximately six months, the second suspension has stood for at least approximately six months and the third suspension has stood for at least approximately six months.

3. The ointment of claim 1, wherein the alcohol solvent in one or more of the three suspensions is rubbing alcohol.

4. The ointment of claim 1, wherein to alcohol solvent in one or morn of the three suspensions is ethyl alcohol.

5. The ointment of claim 1, wherein the alcohol solvent in one or more of the three suspensions is isopropyl alcohol.

6. The ointment of claim 1, wherein the first suspension is in a proportion of peels of approximately six oranges per one quart of container containing the orange peels and alcohol solvent, the second suspension is in a proportion of peels of approximately six banana per one quart of container containing the banana peels and alcohol solvent, and to third suspension is in a proportion of peels of approximately six apples per one quart of container containing the apple peels and alcohol solvent.

7. A method of creating an ointment useful in the treatment of arthritis and/or gout, comprising:
    placing into a first container a first quantity of peels of apples so as to obtain a proportion of at least approximately 6 apple peels for each quart of capacity of the first container,
    filling the first container with an alcohol solvent,
    placing into a second container a second quantity of peels of bananas so as to obtain a proportion of at least approximately 6 banana peels for each quart of capacity of the second container,
    filling the second container with an alcohol solvent,
    placing into a third container a third quantity of peels of oranges so as to obtain a proportion of at least approximately 6 orange peels for each quart of capacity of the second container,
    filling the third container with an alcohol solvent,
    allowing the first container, the second container and the third container to stand for at least approximately five months,
    removing a first clear liquid from a solid residue in the first container,
    removing a second clear liquid from a solid residue in the second container,
    removing a third clear liquid from a solid residue in the third container, and
    thoroughly inking the first clear liquid, the second clear liquid and the third clear liquid together to obtain a liquid ointment.

8. The method of claim 7, wherein the first container, the second container and the third container are allowed to stand for at least approximately 6 months.

9. The method of claim 7, wherein the first, second and third containers are monitored during the at least approximately five months and wherein any reductions in alcohol solvent are replenished by addition of alcohol solvent so that the first, second and third containers are kept full.

10. The method of claim 7, wherein the alcohol solvent is rubbing alcohol.

11. The method of claim 7, wherein the alcohol solvent is ethyl alcohol.

12. The method of claim 7, wherein the alcohol solvent is isopropyl alcohol.

13. The method of claim 7, wherein the first quantity of peels of apples is placed into the first container so as to obtain a proportion of approximately 6 apple peels for each quart of capacity of the first container, wherein the second quantity of peels of bananas is placed into the second container so as to obtain a proportion of approximately 6 banana peels for each quart of capacity of the second container, and wherein the third quantity of peels of oranges is placed into the third container so as to obtain a proportion of approximately 6 orange peels for each quart of capacity of the third container.

14. A method of treating arthritis and/or gout comprising:

placing into a first container a first quantity of peels of apples so that a proportion of at least approximately 6 apple peels for each quart of capacity of the first container is maintained, filling the first container with an alcohol solvent, placing into a second container a second quantity of peels of bananas so that a proportion of at least approximately 6 banana peels for each quart of capacity of the first container is maintained, filling the second container with an alcohol solvent, placing into a third container a third quantity of peels of oranges so that a proportion of at least approximately 6 orange peels for each quart of capacity of the first container is maintained, filling the third container with an alcohol solvent, allowing the first container, the second container and the third container to stand for at least approximately five months, removing a first clear liquid from a solid residue in the first container, removing a second clear liquid from a solid residue in the second container, removing a third clear liquid from a solid residue in the third container, and thoroughly mixing the first clear liquid, the second clear liquid and the third clear liquid together to obtain a liquid ointment, and topically applying the liquid ointment to an affected area of a skin of the human.

\* \* \* \* \*

UNITED STATES PATENT AND TRADEMARK OFFICE
CERTIFICATE OF CORRECTION

PATENT NO. : 7,147,875 B2 Page 1 of 1
APPLICATION NO. : 11/034368
DATED : December 12, 2006
INVENTOR(S) : Pridgen It is certified that error appears in the above-identified patent and that said Letters Patent is hereby corrected as shown below:

Title Page; Please insert;
(74) Attorney, Agent, or Firm - Steven Horowitz

Signed and Sealed this

Ninth Day of October, 2007

JON W. DUDAS
*Director of the United States Patent and Trademark Office*